(12) United States Patent
Burkett

(10) Patent No.: US 7,462,346 B2
(45) Date of Patent: Dec. 9, 2008

(54) LIGHT-STABILIZED(IN VIVO) STAIN COMPOSITION AND METHOD OF MANUFACTURE

(75) Inventor: Douglas D. Burkett, Gilbert, AZ (US)

(73) Assignee: Zila Biotechnology, Inc., Phoenix, AZ (US)

( * ) Notice: Subject to any disclaimer, the term of this patent is extended or adjusted under 35 U.S.C. 154(b) by 387 days.

(21) Appl. No.: 10/487,329

(22) PCT Filed: Aug. 28, 2001

(86) PCT No.: PCT/US01/26805

§ 371 (c)(1),
(2), (4) Date: Feb. 17, 2004

(87) PCT Pub. No.: WO03/020323

PCT Pub. Date: Mar. 13, 2003

(65) Prior Publication Data

US 2004/0247695 A1    Dec. 9, 2004

(51) Int. Cl.
*A61B 10/00* (2006.01)
*A61B 5/00* (2006.01)
*A61B 8/00* (2006.01)

(52) U.S. Cl. .................. 424/9.6; 424/1.11; 424/1.65; 544/34; 544/36

(58) Field of Classification Search ............... 424/1.11, 424/1.65, 9.1, 9.6, 9.7, 9.8; 544/1, 3, 35, 544/37, 34, 36
See application file for complete search history.

(56) References Cited

U.S. PATENT DOCUMENTS

| | | | | |
|---|---|---|---|---|
| 4,321,251 A * | 3/1982 | Mashberg | .................... | 424/9.7 |
| 6,086,852 A * | 7/2000 | Burkett | ...................... | 424/9.7 |
| 6,194,573 B1 * | 2/2001 | Burkett | ...................... | 544/37 |
| 6,372,904 B2 * | 4/2002 | Burkett | ...................... | 544/37 |
| 6,830,743 B1 * | 12/2004 | Burkett | ...................... | 424/9.7 |
| 2004/0247695 A1 * | 12/2004 | Burkett | ...................... | 424/600 |

OTHER PUBLICATIONS

Havelcova e tal (Dyes and pigments, 2000, vol. 44, pp. 49-54).*
Havelcova et al (Dyes and Pigments, 2000, vol. 44, pp. 49-54).*

* cited by examiner

*Primary Examiner*—D. L Jones
(74) *Attorney, Agent, or Firm*—Jeffer Mangels Butler & Marmaro LLP

(57) ABSTRACT

Photochemical demethylation reactions in solutions of thiazine dyes, in which the dye molecules act as both sensitizer and substrate, are reduced by quenching triple-state dye molecules, returning them to the unreactive ground state.

1 Claim, No Drawings

LIGHT-STABILIZED(IN VIVO) STAIN COMPOSITION AND METHOD OF MANUFACTURE

This invention relates to light-stabilized thiazine dye biological stain compositions, illustratively, the tolonium chloride ("TC") dye compositions disclosed in my U.S. Pat. No. 6,086,852.

In another respect the invention concerns methods of manufacturing such compositions.

In particular the invention contemplates light-stabilized tolonium chloride ("TC") dye compositions and their manufacture.

BACKGROUND OF THE INVENTION

As far as known, prior workers, such as Mashberg (U.S. Pat. No. 4,321,251), who instigated the use of TC for in vivo identification of dysplasia, used prior art dye products in which the conformational isomers of TC plus the N-demethylation and N,N-demethylation derivatives of the conformational isomers were less than 80% of the dye composition and in which the two N-demethylation derivatives of the conformational isomers, formed greater than about 20% % of the dye composition. According to my information, prior workers were unaware of the exact composition of their "TC" products and manufacturers of prior art TC products were unable to reproducibly prepare them. In fact, the prevalent literature description of the quality of TC was simply that it have "good color value". The Biological Stain Commission specifies an analytical titration procedure for determining only the "organic dye content" of the TC material. The prior art use of such loosely defined "TC" resulted in anomalous clinical observations and serious problems in obtaining necessary regulatory clearances to manufacture and market such products for use in human diagnostic procedures.

In addition to the problem of variable initial composition, prior art TC and other thiazine biological stains were subject to time-related variations in composition. For example, Dean et al. in "Stains Technology", Vol. 32, No. 1, pp. 35 et seq. (1977) recommended that thiazine dyes in methanolic solutions should be refrigerated to prevent further oxidative N-demethylation. Liao, et al. reported in "Stains Technology", Vol. 57, No. 1, pp. 23 et seq. (1982) that reduction in methylene blue content by precipitation from methanolic Wright's stain solution could be markedly decreased by simultaneous addition of diethylamine hydrochloride and dimethylamine hydrochloride.

In my U.S. Pat. No. 6,086,852, I describe a process for reproducibly manufacturing high-quality TC products initially having a high proportion of the conformational isomers with respect to the N-demethylation products of such isomers. While exclusion of contact with air and avoidance of high temperatures retard oxidative N-demethylation of the conformational isomers, it is observed that, in the absence of free radical scavengers, such as metal ions, alcoholic solutions of this TC product undergo light-induced or photochemical N-demethylation.

BRIEF DESCRIPTION OF THE INVENTION

I have now discovered improvements in solutions of thiazine dyes, wherein molecules of the dye act as both the sensitizers and substrates in photochemical oxidative N-demethylation reactions, in which reactions some of said dye molecules absorb light and are converted to the singlet state, some of said singlet-state dye molecules react with unactivated substrate dye molecules to form triplet state molecules by intersystem crossing, some of said triplet-state molecules react with ambient ground-state oxygen to produce singlet-state oxygen molecules, and some of said singlet-state oxygen molecules demethylate ground-state dye molecules. My improvements, which substantially reduce said demethylation comprises quenching at least some of the triplet-state dye, preferably by incorporating into said solution a free radical scavenger, e.g., a metal ion, thus returning the triplet-state dye molecules to the unreactive ground-state.

DETAILED DESCRIPTION OF THE INVENTION

Oxidative N-demethylation of a thiazine dye is envisioned to occur as illustrated below for the demethylation of TC:

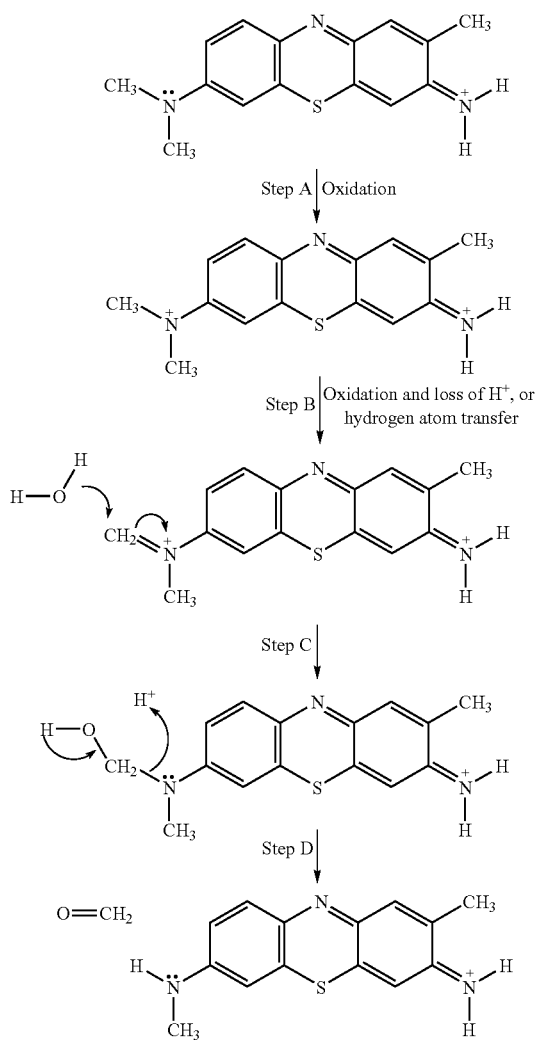

In Steps A and B, an electron is removed from the TC to produce a radical cation, which is then oxidized again and loses a proton to form an iminium ion. Subsequently, the iminium ion undergoes nucleophilic attack by water (Step C) to produce the carbinolamine intermediate, in which there is a hydroxyl group and an amino group attached to the same carbon atom. The carbinolamine is unstable, and loss of the amine (Step D) liberates formaldehyde and monodemethylated TC. In the case of demethylation of methylene blue, this would correspond to the formation of Azure C from Azure A.

In photochemical demethylation reactions, TC apparently acts both as the sensitizer and the substrate in photochemical reactions, i.e., in the absence of free-radical scavengers, it brings about its own photodecomposition. Thus, TC absorbs light and becomes a "photosensitizer" and brings about a direct reaction of the TC in its singlet excited state with another TC molecule "substrate." The substrate molecule reacts with the triplet state of the dye, formed by intersystem crossing (isc). Singlet oxygen is formed by reaction of ground state oxygen with the triplet state of the dye, followed by reaction of singlet oxygen with the substrate.

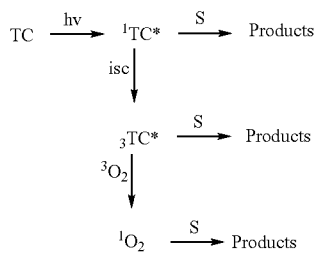

The "heavy atom" effect of a metal ion, such as zinc, sodium, and the like, quenches the triplet state of the dye, returning it to its unreactive ground singlet state, preventing the triplet state from participation in the degradation reactions.

The amounts of metal ion required to provide high photochemical stability are not highly critical and can be determined by routine experimentation having regard for this disclosure. In general, I prefer to employ upward of about 4 wt. % zinc or 9 wt. % sodium or both in the dye solution, although greater amounts are not harmful and smaller amounts are at least partially effective. The metal content should be a minimum of upwards of 2 wt % for at least partial effectiveness.

EXAMPLES

The following examples illustrates the practice of the preferred embodiments of the invention and are not intended to serve as limitations on the scope thereof, which is defined only in the appended claims.

Example 1

This example illustrates the light-instability of a TC product with negligible content of metal ions.

A sample of the TC product is prepared in accordance with Example 1 of my U.S. Pat. No. 6,086,852, incorporated herein by reference, and further purified by preparative high performance liquid chromatography. The total metal content of this sample is less than 0.2 wt. %.

An aliquout of this purified TC product sample is deep-blue in color. After standing overnight in the laboratory, exposed to ambient incandescent light, the solution becomes colorless.

Example 2

The sample of Example 1 except containing about 4 wt % Zn (as zinc chloride) and 9% Na (as sodium chloride) in the solution is essentially completely stable in the presence of incandescent light.

Example 3

The procedures of Examples 1 and 2 are repeated using methylene blue, Azure A and Azure C instead of TC. Similar results are obtained.

Example 4

The procedures of Example 1-3 are repeated except using only zinc chloride in solution and only sodium chloride in solution. Equivalent results are obtained.

Example 5

The procedures of Example 14 are repeated except that soluble salts of magnesium, chromium and silicon are used instead of zinc and sodium salts. Similar results are obtained.

What is claimed is:

1. A method for at least partially reducing the oxidative demethylation of a thiazine dye, the method comprising the steps of:
   (a) providing a thiazine dye in solution; and
   (b) adding a metal ion to the thiazine dye solution;
      wherein the thiazine dye comprises an inner thiazine ring and two outer rings, wherein at least one of the two outer rings has an -N-methylamino or an -N,N-dimethylamino substituent;
      wherein the metal ion quenches the thiazine dye to at least partially reduce the oxidative demethylation of the thiazine dye; and
wherein the method further comprises the step of purifying the thiazine dye solution by high performance liquid chromatography before the step of adding the metal ion to the thiazine dye solution.

* * * * *